United States Patent [19]

Kato et al.

[11] Patent Number: 4,464,050

[45] Date of Patent: Aug. 7, 1984

[54] APPARATUS FOR DETECTING OPTICALLY DEFECTS

[75] Inventors: Kiichi Kato, Hachioji; Masaharu Sakamoto, Tokyo; Shoji Yoshikawa, Hachioji; Kunio Yamamiya, Tokyo; Hiroshi Kodama; Ken Ohsima, both of Hachioji, all of Japan

[73] Assignee: Olympus Optical Co., Ltd., Japan

[21] Appl. No.: 345,153

[22] Filed: Feb. 2, 1982

[30] Foreign Application Priority Data

Feb. 7, 1981 [JP] Japan .................................. 56-16294

[51] Int. Cl.$^3$ ............................................. G01N 21/88
[52] U.S. Cl. .................................... 356/237; 250/572; 356/446
[58] Field of Search ............... 356/237, 371, 445, 446; 250/563, 572; 369/45, 46, 54

[56] References Cited

U.S. PATENT DOCUMENTS 3,229,564  1/1966  Meltzer .............................. 356/446
4,314,763  2/1982  Steigmeier et al. .................. 356/237

Primary Examiner—Vincent P. McGraw
Attorney, Agent, or Firm—Parkhurst & Oliff

[57] ABSTRACT

An apparatus for detecting optically defects in object such as original glass disc for use in manufacturing video and audio discs by projecting a laser light flux onto the object includes an objective lens for focussing the incident laser light flux onto the object as a small light spot, the laser light flux passing through the objective lens at only its central portion. When the object has no defect in the light spot area, the laser light flux is regularly reflected by the object surface, but when the object includes a defect in the light spot area, the light flux is scattered by the defect. The directly reflected and scattered light fluxes are collected by the objective lens and are then separated from each other by means of a small mirror arranged in an optical axis of the directly reflected light flux. The directly reflected and scattered light fluxes thus separated are received by first and second light detectors. A cylindrical lens is inserted between the small mirror and the first light detector having four divided light receiving regions. The objective lens is driven into an in-focussed position under the control of a focussing error signal which is derived by processing output signals from the four divided light receiving regions. A defect signal is derived by processing output signals supplied from the first and second light detectors.

15 Claims, 13 Drawing Figures

APPARATUS FOR DETECTING OPTICALLY DEFECTS

BACKGROUND OF THE INVENTION

The present invention relates to an apparatus for detecting optically defects in an object by projecting a light beam onto the object and by detecting a variation in the light beam reflected by the object.

In a semiconductor manufacturing field, a quality of a semiconductor wafer must be checked. If there are defects in a ground surface of the semiconductor wafer, a property of finally obtained semiconductor devices might be deteriorated or damaged. Also in the field of manufacturing video and audio discs, an original disc made of glass should not have defects. If the original glass disc has defects in its ground surface, a number of video and audio discs manufactured by the original disc might become defective. Therefore, it is necessary to check the surface condition of the semiconductor wafer and the glass disc after their surfaces have been ground into mirror surfaces.

Usually the checking operation is carried out visually by experienced persons. The visual checking can discriminate the defects from others precisely, but it is difficult to obtain a high reliability due to difference between respective persons and mistakes inherent to the human beings. Further, the operations are subjected to fatigue and efficiency of checking is limited. Moreover, it is difficult to sort or select the detected defects in accordance with their properties or characteristics. Therefore, there has been required to develop an apparatus for detecting defects with high efficiency and reliability.

Heretofore, there have been developed various methods for detecting small defects and fine particles. In the simplest method, the human eyes are replaced by a television camera and an output video signal from the television camera is suitably processed by an electrical circuit to derive a defect signal. However, presently available television cameras do not have a sufficiently high resolving power for detecting small defects. Several types of apparatuses for detecting fine dusts or particles in air have been commercially available. However, these apparatuses use an incandescent lamp as a light source and thus, the maximum resolving power is limited only to about 0.5 $\mu$m and even the highest grade apparatus has the resolving power of 0.2 $\mu$m to 0.3 $\mu$m. In an apparatus for detecting smaller particles, use is made of a laser light source. Since the laser light source can generate a coherent parallel light beam having a very small cross section, a difference between scattered or diffracted light and non-scattered light becomes large and useful information can be derived from a phase component.

FIG. 1 is a schematic view showing the known apparatus for checking a surface condition of a semiconductor wafer by means of the laser light. In FIG. 1, a laser light beam 1 emitted from a laser light source L is reflected by a mirror 2 and is focussed by means of an objective lens 3 onto an object 4 to be checked, i.e. a semiconductor wafer. In order to collect a light flux 7 scattered by a defect in the object 4, a condenser lens 5 is arranged beside the objective lens 3. The collected light flux is made incident upon a light detector 6 which produces an electric signal representing a defect. In order to move the incident light beam with respect to the object 4, the mirror 2 may be swung or the object 4 may be rotated or moved linearly. In this manner the whole surface of the object 4 can be scanned.

However, in such a known apparatus the condenser lens 5 can collect only a small part of the light flux scattered in all directions and therefore, it is difficult to obtain the signal having a high S/N and a detection accuracy is low. Moreover, in order to collect a larger amount of the scattered light, the objective lens 3 must be spaced from the object 4 by a larger distance and must have a longer working distance, and in order to project the bright light beam onto the object 4, the objective lens 3 must have a larger diameter or aperture. Under the above circumstances, in the known apparatus the freedom in designing the objective lens 3 is limited to a great extent.

SUMMARY OF THE INVENTION

The present invention has for its object to provide a novel and useful apparatus for detecting optically defects in objects with a very high accuracy by means of an objective lens which can be designed under a large freedom.

According to the invention, an apparatus for detecting optically defects in objects comprises:

means for emitting a laser light flux having a small diameter;

an objective lens having a diameter larger than said diameter of laser light flux for focussing it onto an object to be checked and for collecting a light flux directly reflected by the object and a light flux scattered by a defect in the object;

first beam splitting means directing the laser light flux emanating from said laser light emitting means toward the objective lens and for directing said directly reflected and scattered light fluxes emanating from the objective lens toward a direction different from a direction to said emitting means;

second beam splitting means for splitting the directly reflected and scattered light fluxes emanating from said first beam splitting means from one another;

first light detecting means for receiving the directly reflected light flux emanating from said second beam splitting means to derive a first output signal;

means for receiving said first output signal to derive a focussing error signal in accordance with a variation in the directly reflected light flux due to a fluctuation in a distance between the objective lens and the object;

means for driving the objective lens into an infocussed position in response to said focussing error signal;

second light detecting means for receiving the scattered light flux emanating from said second beam splitting means to derive a second output signal; and means for receiving at least one of said first and second output signals to produce a detection signal representing an existence of the defects in the object.

DESCRIPTION OF THE PREFERRED EMBODIMENTS

Figure 1:
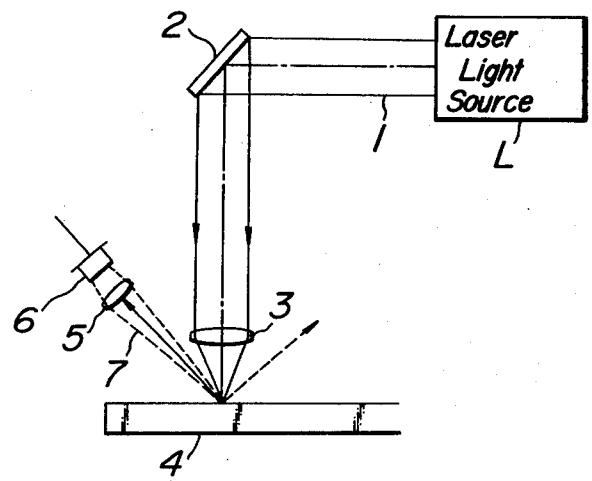
FIG. 1 is a schematic view illustrating a known defect detecting apparatus comprising a laser light source.
Figure 2:
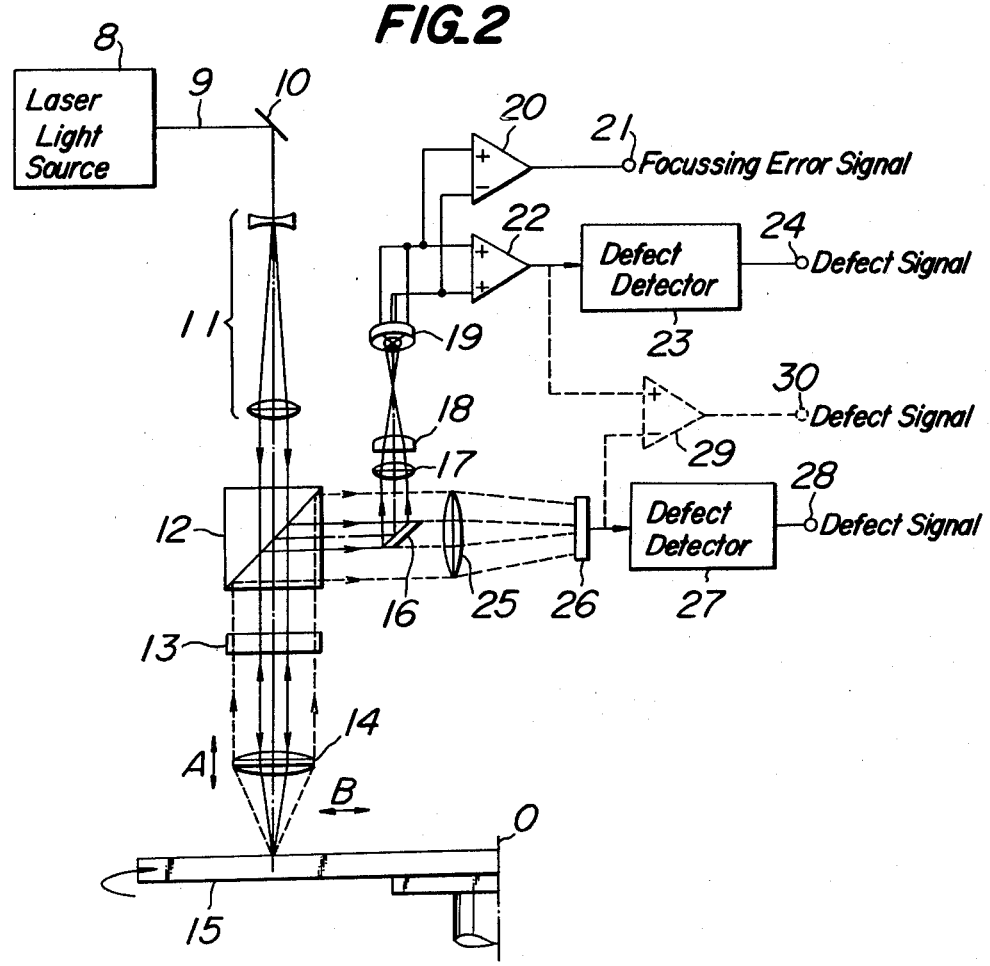
FIG. 2 is a schematic view showing an embodiment of the optical defect detecting apparatus according to the invention.

FIG. 2 is a schematic view showing an embodiment of the defect detecting apparatus according to the invention. A laser light source 8 emits a laser light flux 9 polarized linearly in a plane of the drawing of FIG. 2. The laser light flux 9 is reflected by a mirror 10 and is widened by an expander lens 11 to a suitable diameter. The expanded laser light flux is transmitted through a polarizing beam splitter 12 and a quarter-wavelength plate 13 and is then focussed by an objective lens 14 as a small light spot onto an object 15 which is rotated about an axis O. The laser light beam impinging upon the object 15 is reflected by it. When there is no defect in the light spot area, the laser light flux is regularly reflected in a light cone identical with the cone of the incident light flux. This reflected light flux is, herein, termed as a directly reflected light flux. The directly reflected light flux is transmitted through the objective lens 14 and the quarter-wavelength plate 13 and is made incident upon the polarizing beam splitter 12. According to the invention the diameter of the incident light flux is made smaller than a diameter of the objective lens 14, so that the incident light flux occupies only a part of an iris of the objective lens 14.

When a defect is existent in the light spot area, the incident laser light flux is scattered by the defect in all directions. A large part of the scattered light flux denoted by dotted lines are collected by the objective lens 14 and is made incident upon the polarizing beam splitter 12 through the quarter-wavelength plate 13. The directly reflected light flux and scattered light flux impinging upon the polarizing beam splitter 12 have passed through the quarter-wavelength plate 13 twice and thus, are reflected by the polarizing light splitter 12 toward a direction different from that to the laser light source 8. The directly reflected light flux emanating from the beam splitter 12 is reflected upward by a small mirror 16 serving as a second beam splitting element and is made incident upon a first light detector 19 having four divided light receiving regions by means of a lens 17 and a cylindrical lens 18. Sum signals of the light receiving regions arranged in diagonal directions are supplied to a differential amplifier 20 to derive a difference between these sum signals as a focussing error signal representing a deviation of the objective lens 14 from an in-focussed condition. The focussing error signal thus derived is supplied to a suitable actuator not shown to drive the objective lens 14 in its optical axis direction as shown by a double-headed arrow A in such a manner that the focussed light spot is always projected onto the object 15. In the present embodiment, the focussing error signal is detected by means of an astigmatism aberration due to the cylindrical lens 18. Such a focussing error detecting method has been used in a video disc player.

When the light beam impinges upon the defect in the object 15, the amount of light flux received by the first detector 19 is decreased to a great extent due to scattering. Therefore by deriving a sum of the output signals from the four light receiving regions of the detector 19 by means of an adder 22 and by detecting a variation of the sum signal in a defect detecting circuit 23, it is possible to produce a defect signal at an output terminal 24. In this case, since the amount of the directly reflected light flux is changed largely in accordance with the defect, the sum signal from the adder 22 can have an extremely high S/N and therefore, the detection of defect can be effected in a very accurate and reliable manner.

The scattered light flux emanating from the beam splitter 12 is made incident upon a second light detector 26 via a condenser lens 25. The detector 26 produces a large signal when the defect is scanned and thus, by supplying an output signal from the detector 26 to a defect detecting circuit 27, it is also possible to produce a defect signal at an output terminal 28. As will be explained later, it is possible to detect size, character, etc. of the defects by suitably constructing the second light detector 26. Further, according to the invention, a defect signal may be derived from both the output signals of the first and second light detectors 19 and 26. For instance, as shown by dotted lines in FIG. 2, these output signals may be supplied to a differential amplifier 29 and a defect signal having a higher S/N may be obtained at an output terminal 30.

In order to scan the whole surface of the object 15, the object 15 is rotated about the axis O and at the same time an optical system is moved in a radial direction with respect to the object 15 as shown by a double-headed arrow B. Such driving mechanisms are provided in the usual video and audio disc players and thus detailed explanation thereof is omitted here.

Figure 3A:
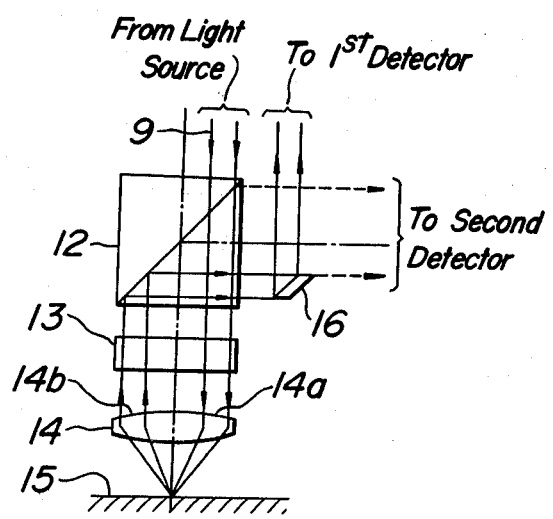
FIGS. 3A and 3B are side and plan views, respectively depicting an embodiment of an optical system provided in the apparatus according to the invention.
Figure 3B:
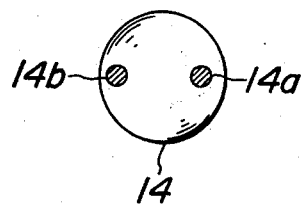

FIGS. 3A and 3B show a modified embodiment of the optical system provided in the defect detecting apparatus according to the invention. In the present embodiment, an optical axis of the indicent laser light flux 9 is not made identical with the optical axis of objective lens, but is shifted rightward. Therefore, the incident light flux 9 is transmitted through a right hand portion 14a of the objective lens 14 and the directly reflected light flux is transmitted through a left hand portion 14b of the objective lens 14. When the incident light flux impinges upon a defect in the object 15, the scattered light flux are made incident upon the whole surface of objective lens 14. The directly reflected light flux reflected by the polarizing beam splitter 12 is further reflected by the small mirror 16 toward the first light detector 19 not shown in FIG. 3A, and the scattered light flux reflected by the beam splitter 12 is made incident upon the second light detector also not shown in FIG. 3A. In this manner, by detecting the variation in a light amount of the directly reflected light flux impinging upon the first light detector and/or the scattered light flux impinging upon the second light detector, the defect signal can be obtained in a highly precise and reliable manner.

Figure 4A:
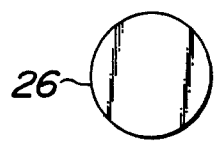
FIGS. 4A and 4B are plane views showing a light detector for receiving a scattered light flux.
Figure 5:
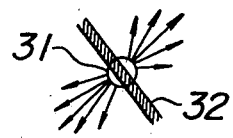
FIG. 5 is a schematic view illustrating a scattering condition due to a defect having a directional property.
Figure 4B:
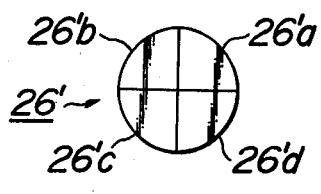

FIGS. 4A and 4B show two embodiments of the second light detector 26 for receiving the light flux scattered by the defect in the object. In the embodiment shown in FIG. 4A, the light detector 26 comprises a single light receiving region, but in the embodiment illustrated in FIG. 4B the light detector 26' has four light receiving regions 26'a to 26'd divided in orthogonal directions. The divided light detector 26' is preferably used for detecting the light flux scattered by a defect 31 having a directional property as shown in FIG. 5. In FIG. 5, a hatched strip 32 denotes a locus traced by the light beam spot. In such a case, by suitably processing output signals from the four light receiving regions 26'a to 26'd, it is possible to determine direction, size and characteristic of defects.

Figure 6:
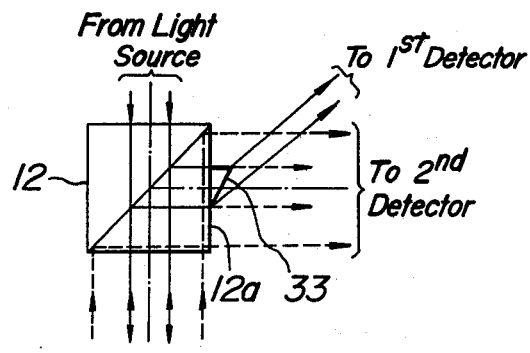
FIGS. 6 and 7 are schematic views showing another embodiments of the optical system in the apparatus according to the invention.
Figure 8:
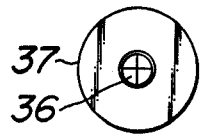
FIG. 8 is a plan view illustrating a light detector provided in the optical system shown in FIG. 7.
Figure 7:
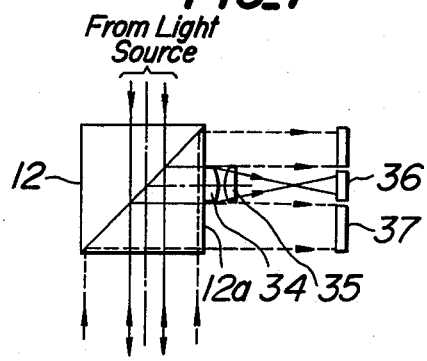

FIGS. 6 and 7 illustrate another embodiment of the optical system of the defect detecting apparatus according to the invention, and FIG. 8 is a plan view showing first and second light detectors provided in the optical system illustrated in FIG. 7. In the embodiment shown in FIG. 6, a small prism 33 is applied to an exit surface 12a of the polarizing beam splitter 12 at such a position that the directly reflected light beam is made incident upon the prism 33. Then the directly reflected light beam is refracted by the prism 33 into a different direction from that into which the scattered light beam propagates, and impinges upon the first light detector. In the embodiment shown in FIG. 7, a lens 34 is applied to an exit surface 12a of the polarizing beam splitter 12 at such a position that the directly reflected light beam is converged by the lens 34. The converged light beam is then transmitted through a cylindrical lens 35 and is further made incident upon a first light detector 36 having four divided light receiving regions as shown in FIG. 8. The scattered light flux is made incident upon a ring-shaped second light detector 37.

Figure 9:
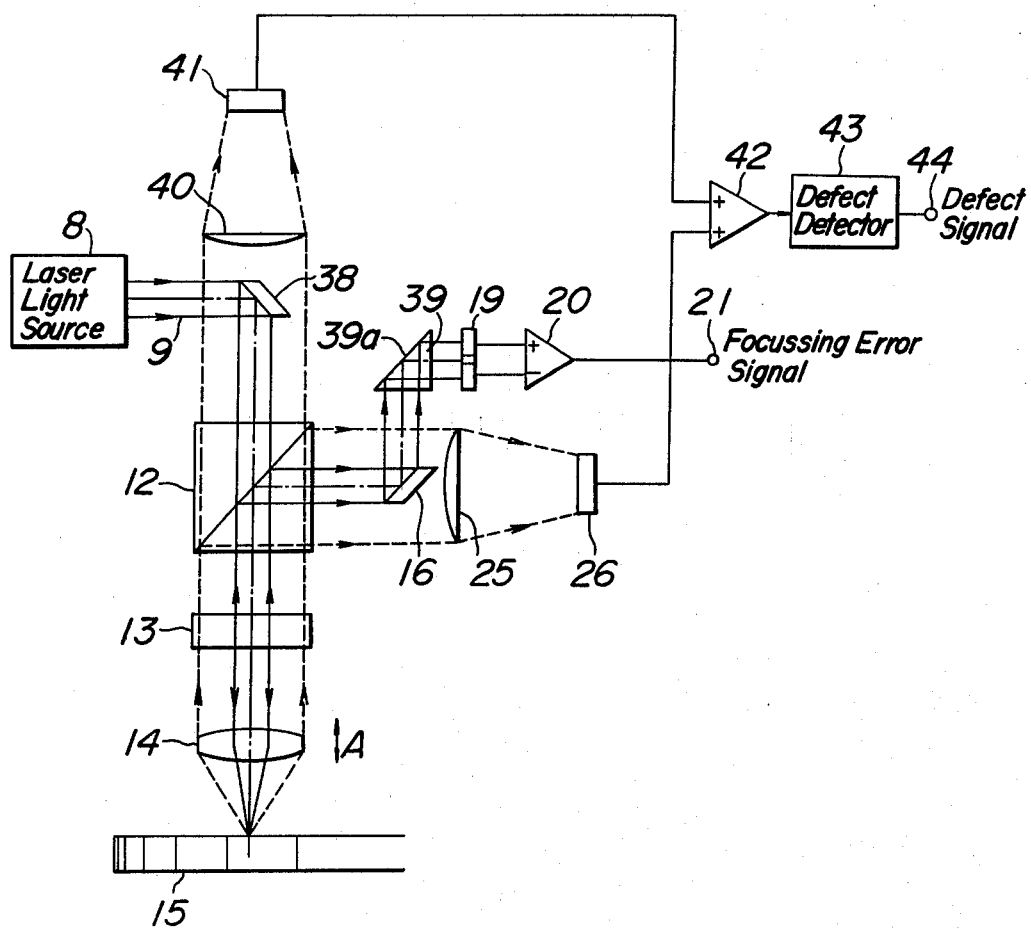
FIG. 9 is a schematic view of the defect detecting apparatus according to the invention.

FIG. 9 is a schematic view showing another embodiment of the defect detecting apparatus according to the invention. In this embodiment, portions similar to those shown in FIG. 2 are denoted by the same reference numerals used in FIG. 2. A parallel laser light flux 9 emitted from a laser light source 8 is reflected by a partially reflecting mirror 38 and then is made incident upon an object 15 via a polarizing beam splitter 12, a quater-wavelength plate 13 and an objective lens 14. The light flux directly reflected by the object 15 is collected by the objective lens 14 and is then made incident upon the beam splitter 12 via the quarter-wavelength plate 13. The directly reflected light flux reflected by the beam splitter 12 is further reflected by a small mirror 16 and impinges upon a prism 39 having a reflection surface 39a which is so set that in the in-focussed condition, the light beam is made incident upon the surface 39a at an incident angle substantially equal to a critical angle. The light beam reflected by the surface 39a of the prism 39 is received by a first light detector 19 having two light receiving regions divided along a boundary perpendicular to the plane of drawing. By deriving a difference between output signals from the two light receiving regions by means of a differential amplifier 20, it is possible to obtain at an output terminal 21 a focussing error signal. By driving the objective lens 14 in response to the focussing error signal in a direction of its optical axis as shown by a double-headed arrow A, the objective lens 14 can be always positioned at the in-focussed position. Such focussing error detection method and objective lens driving method having been fully explained in copending U.S. patent applications Ser. Nos. 195,075, 292,929 and 292,930. When the incident light flux is focussed at a defect on the object 15, the light beam is scattered. In general, the laser light beam scattered by the defect becomes an elliptically polarized light and thus, a part of the scattered light flux impinging upon the polarizing beam splitter 12 is transmitted therethrough. This transmitted light is collected by a condenser lens 40 and is made incident upon a third light detector 41. The scattered light flux reflected by the polarizing beam splitter 12 is collected by a lens 25 and impinges upon a second light detector 26 like as the previous embodiment. Then output signals from the second and third light detectors 26 and 41 are combined in an adder 42 and a sum signal thus obtained is supplied to a defect detecting circuit 43 which generates a defect signal at an output terminal 44. In this manner, according to the present embodiment, the defects in the object can be detected much more accurately with a much higher sensitivity.

Figure 10:
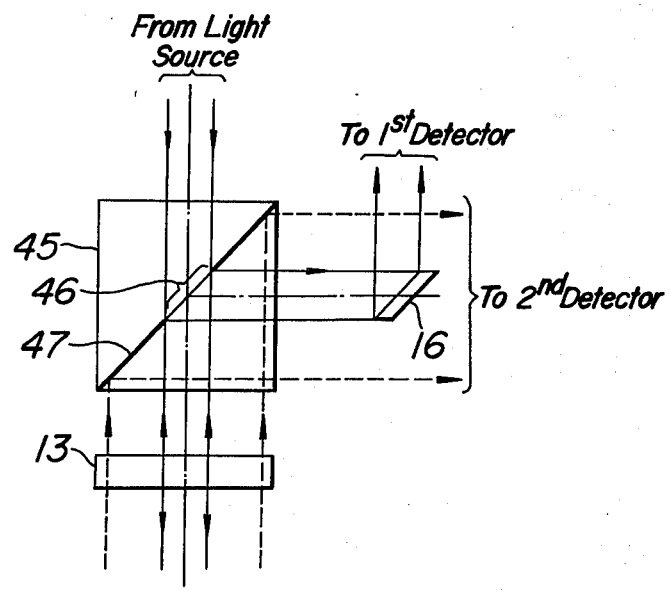
FIG. 10 is a side view illustrating another embodiment of the optical system of the defect detecting apparatus according to the invention.

FIG. 10 shows another embodiment of the optical system provided in the defect detecting apparatus according to the invention. In this embodiment, a beam splitting element 45 comprises a polarizing surface portion 46 and a reflecting surface portion 47 formed between prism halves. The incident laser light flux is transmitted through the polarizing surface portion 46 and the directly reflected light flux is reflected by the polarizing surface portion 46 toward a small mirror 16. Almost all scattered light flux is reflected by the reflection surface portion 47 even if the scattered light flux is polarized elliptically.

Figure 11:
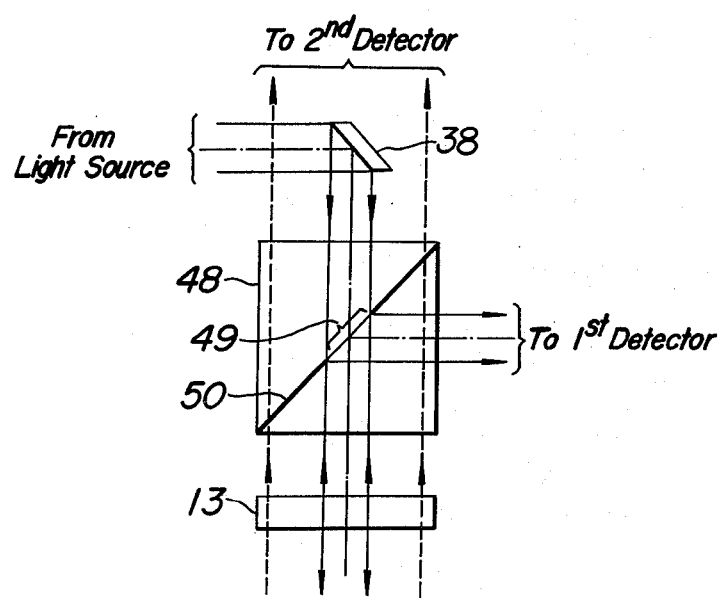
FIG. 11 is a side view showing still another embodiment of the defect detecting apparatus according to the invention.

FIG. 11 illustrates still another embodiment of the optical system according to the invention. In this embodiment, a beam splitting element 48 comprises a polarizing surface portion 49 through which the incident light beam is transmitted and by means of which the directly reflected light flux is reflected toward the first light detector not shown. A remaining surface portion 50 is formed by a cementing agent such as balsam. Therefore, the scattered light flux can be freely transmitted through the surface portion 50 toward the second light detector not shown.

In the optical systems shown in FIGS. 10 and 11, there may be attained the same effect as that achieved by the embodiment illustrated in FIG. 9 without providing the third light detector 41 for receiving the scattered light flux and thus, the construction becomes much simpler.

As explained above in detail, according to the invention the laser light beam is focussed onto the object by the objective lens which also serves to collect the directly reflected and scattered light fluxes, and these light fluxes are detected separately from each other to detect the defect in the object. Therefore, the large amount of the directly reflected and scattered light fluxes can be effectively collected by the single objective lens and the defect detection can be carried out with the very high sensitivity and accuracy. Further, since the objective lens can be arranged near the object and there is no limitation for the working distance, the freedom of design of the objective lens can be increased to a great extent.

What is claimed is:

1. An apparatus for detecting optically defects in objects comprising
   means for emitting a laser light flux having a small diameter;

an objective lens having a diameter larger than said diameter of laser light flux for focussing it onto an object to be checked and for collecting a light flux directly reflected by the object and a light flux scattered by a defect in the object;

first beam splitting means directing the laser light flux emanating from said laser light emitting means toward the objective lens and for directing said directly reflected and scattered light fluxes emanating from the objective lens toward a direction different from a direction to said emitting means;

second beam splitting means for splitting the directly reflected and scattered light fluxes emanating from said first beam splitting means from one another;

first light detecting means for receiving the directly reflected light flux emanating from said second beam splitting means to derive a first output signal;

means for receiving said first output signal to derive a focussing error signal in accordance with a variation in the directly reflected light flux due to a fluctuation in a distance between the objective lens and the object;

means for driving the objective lens into an in-focussed position in response to said focussing error signal;

second light detecting means for receiving the scattered light flux emanating from said second beam splitting means to derive a second output signal; and means for receiving at least one of said first and second output signals to produce a defect signal representing an existence of the defects in the object.

2. An apparatus according to claim 1, wherein said first beam splitting means comprises a polarizing beam splitter arranged between the emitting means and the objective lens and a quarter-wavelength plate arranged between the polarizing beam splitter and the objective lens.

3. An apparatus according to claim 1, wherein said laser light flux emitting means and objective lens are so arranged that the incident laser light flux and the directly reflected laser light flux pass through the objective lens along its optical axis.

4. An apparatus according to claim 1, wherein said laser light flux emitting means and objective lens are so arranged that the incident laser light flux passes through the objective lens at its one side portion and the directly reflected light flux passes through the objective lens at its other side portion which is situated opposite to said one side portion with respect to an optical axis of the objective lens.

5. An apparatus according to claim 2, wherein said second beam splitting means comprises a small mirror for reflecting the directly reflected light flux toward said first light detector.

6. An apparatus according to claim 2, wherein said second beam splitting means comprises a small prism for refracting the directly reflected light flux toward said first light detecting means.

7. An apparatus according to claim 6, wherein said prism is applied to said polarizing beam splitter at a portion from which the directly reflected light flux emanates.

8. An apparatus according to claim 2, wherein said second beam splitting means comprises a small lens for converging the directly reflected light flux toward the first light detecting means.

9. An apparatus according to claim 8, wherein said second light detecting means has a ring-shaped light receiving region arranged concentrically around said first light detecting means.

10. An apparatus according to claim 1, wherein said second beam splitting means comprises a cylindrical lens, said first light detecting means comprises four light receiving regions divided in orthogonal directions, and said focussing error signal generating means comprises a differential amplifier which produces as the focussing error signal a difference between two sums of output signals from diagonally aligned light receiving regions.

11. An apparatus according to claim 1, wherein said second beam splitting means comprises a prism having a reflection surface which is so set that in the in-focussed condition the directly reflected light flux impinges upon the reflection surface at an incident angle substantially equal to a critical angle, said first light detecting means comprises two light receiving regions divided along a plane perpendicular to an incident plane of said reflection surface, and said focussing error signal generating means comprises a differential amplifier which produces a difference between output signals from said two light receiving regions.

12. An apparatus according to claim 2, further comprising third light detecting means for receiving a part of the scattered light flux which emanates from said polarizing beam splitter in the direction toward the laser light emitting means, to produce a third output signal and means for adding said third output signal to said second output signal to generate a sum output signal which is supplied to said defect signal generating means.

13. An apparatus according to claim 12, further comprising means arranged between said polarizing beam splitter and said emitting means and third light detecting means for separating the incident laser light flux from said part of the directly reflected light flux emanating from said polarizing beam splitter.

14. An apparatus according to claim 2, wherein said polarizing beam splitter comprises two rectangular prisms, a polarizing surface portion formed in a part of an interface between said two rectangular prisms and a mirror surface portion formed in the remaining part of said interface.

15. An apparatus according to claim 2, wherein said polarizing beam splitter comprises two rectangular prisms, a polarizing surface portion formed in a part of an interface between said two rectangular prisms and a transparent surface portion formed in the remaining part of said interface.

* * * * *